(12) United States Patent
Radziszewski et al.

(10) Patent No.: US 7,677,079 B2
(45) Date of Patent: Mar. 16, 2010

(54) METHOD AND DEVICE FOR SENSING WEAR

(75) Inventors: Peter Radziszewski, Baie d'Urfe (CA); Sudarshan Martins, Montreal (CA); Coleman Benson, Dollard-des-Ormeaux (CA)

(73) Assignee: McGill University, Montreal (CA)

( * ) Notice: Subject to any disclaimer, the term of this patent is extended or adjusted under 35 U.S.C. 154(b) by 397 days.

(21) Appl. No.: 10/598,412

(22) PCT Filed: Feb. 25, 2005

(86) PCT No.: PCT/CA2005/000285

§ 371 (c)(1),
(2), (4) Date: Aug. 28, 2006

(87) PCT Pub. No.: WO2005/083411

PCT Pub. Date: Sep. 9, 2005

(65) Prior Publication Data

US 2007/0163325 A1 Jul. 19, 2007

Related U.S. Application Data

(60) Provisional application No. 60/547,768, filed on Feb. 27, 2004.

(51) Int. Cl.
*G01N 3/56* (2006.01)
(52) U.S. Cl. .......................................................... 73/7
(58) Field of Classification Search ................ 73/86, 73/768, 763, 7, 8
See application file for complete search history.

(56) References Cited

U.S. PATENT DOCUMENTS

| | | | | |
|---|---|---|---|---|
| 3,314,618 A | * | 4/1967 | McDonald | ................... 241/299 |
| 4,655,077 A | * | 4/1987 | Purvis et al. | ................... 73/86 |
| 4,884,434 A | * | 12/1989 | Satake et al. | ...................... 73/7 |
| 4,945,770 A | | 8/1990 | Alvelid et al. | |
| 5,758,970 A | | 6/1998 | Aubert | |
| 6,366,201 B1 | * | 4/2002 | Hanisko | ..................... 340/454 |
| 6,471,449 B1 | * | 10/2002 | Kataoka | ..................... 407/119 |
| 6,510,729 B2 | | 1/2003 | Bonnevie et al. | |
| 2001/0001236 A1 | * | 5/2001 | Lake | ....................... 340/573.2 |
| 2006/0011452 A1 | * | 1/2006 | Swinderman et al. | ....... 198/497 |

FOREIGN PATENT DOCUMENTS

| | | |
|---|---|---|
| DE | 3915996 C1 | 6/1990 |
| DE | 4231107 A1 | 3/1994 |
| DE | 4308272 C1 | 6/1994 |
| DE | 4312354 C1 | 6/1994 |
| EP | 0369087 B1 | 6/1994 |
| EP | 1052423 A3 | 11/2000 |
| FR | 2599831 A1 | 6/1986 |
| GB | 2192949 A | 1/1988 |
| WO | WO-93/00997 A1 | 1/1993 |
| WO | WO-9506205 A1 | 3/1995 |
| WO | WO-0045066 A1 | 8/2000 |

* cited by examiner

*Primary Examiner*—John Fitzgerald
(74) *Attorney, Agent, or Firm*—Goudreau Gage Dubuc (57) ABSTRACT

A sensor for detecting erosion of a wear surface of a component, particularly a liner attached to the mill shell of a rotating grinding mill. The sensor comprises a conductive element embedded in the component, the conductive element comprising a first end positioned at a first distance from the wear surface, at least one conductive loop comprising a wear portion positioned at a second distance from the wear surface proximate to the first end and a circuit coupled to the at least one element for determining a continuity of the conductive loop.

14 Claims, 9 Drawing Sheets

ID FOR SENSING
METHOD AND DEVICE FOR SENSING WEAR

The present invention claims the benefit of a commonly assigned provisional application entitled "Wear Sensor", which was filed on Feb. 27, 2004 and assigned the Ser. No. 60/547,768. The entire contents of the foregoing provisional patent application are hereby incorporated by reference.

FIELD OF THE INVENTION

The present invention relates to a method and device for sensing wear. In particular, the present invention relates to a wear sensor for sensing the erosion of a wear surface of a component.

BACKGROUND TO THE INVENTION

Ores that are mined from the ground are obtained in a wide variety of sizes of particulates, varying from relatively small sizes to large chunks of mineralized material. The ore must be reduced to a size of particulate into a fine sieve range that is suitable for flotation where, through the use of suitable additives, the ore bearing particles are separated from the gangue.

One technique used by the mining industry to affect the requisite reduction in particulate size is to crush or grind the ore in a rotating grinding mill. As the mill rotates, the ore is lifted up by lifters and then dropped back onto itself. The impact causes the ore to be crushed, cracked, broken or otherwise formed into smaller particulates. Continued action in this manner causes a successive reduction in the size of the particulates which can be removed subsequent once a sufficiently small size has been achieved. The process is relatively continuous, with rough ore being fed at one end of the rotating mill and fine particulates being removed from the other.

In view of the abrasive character of the material being ground, the wear on the inside of the mill is a serious problem. Typically, such mills are lined with cast or wrought abrasion resistant ferrous alloy liners of several inches thick, or in some cases, with rubber or ceramic liners. These liners are typically in sections, with various configurations, usually being held in place by bolts which hold the liner tightly against the interior of the mill.

During service, the liners are worn by the abrasive action of the minerals being ground in the mill. The speed of wear can vary with a number of factors, including the nature of the ore bodies, which are typically irregular. Additionally, the configuration of the surface of the liner, during its service life, is an important consideration affecting both the life of the liner and the grinding efficiency or grinding rate of the mill. As a result, it is difficult to predict accurately the best time to replace the liners. Indeed, one problem with prior art mills is that in order to assess the current state of wear of the liners, the mill must be stopped, cleaned and a physical examination of the liners take place.

As commercial scale mills are quite large, and process many tons of ore per hour, regularly halting the process and cleaning the mill to determine the state of wear of the liners is impractical. Additionally, in cases of excessive liner wear, increasingly the abrasive particulate matter forms a slurry which races down the inside of the mill shell. Such slurry racing leads to greater abrasive forces being brought to bear on the inside of the mill shell, which can quickly lead to major damage of the mill shell.

SUMMARY OF THE INVENTION

In order to address the above and other drawbacks, there is disclosed a sensor for detecting erosion of a wear surface of a component. The sensor comprises a conductive element embedded in the component, the conductive element comprising a first end positioned at a first distance from the wear surface, at least one conductive loop comprising a wear portion positioned at a second distance from the wear surface proximate to the first end and a circuit coupled to the at least one element for determining a continuity of the conductive loop.

There is also disclosed a sensor for detecting erosion of a wear surface of a component. The sensor comprises at least one conductive trace on a substrate, the substrate attached to the component such that a wearing portion of the trace between a first trace end and a second trace end comes within a predetermined distance from the wear surface, and a circuit for sensing when the first end is isolated from the second end.

Furthermore, there is disclosed a sensor network for sensing uneven wear in a wear surface of a component. The network comprises a plurality of wear sensors distributed through out the component. Each of the sensors comprises at least one signal relaying loop embedded in the lifter and comprising a wear portion positioned at a wear distance from the wear surface and a circuit for sensing a continuity of the at least one loop.

Additionally, there is disclosed a lifter for use in a liner of a grinding mill. The lifter comprises a wear surface and at least one wear sensor. The wear sensor comprises at least one signal relaying loop embedded in the lifter and comprising a wear portion positioned at a wear distance from the wear surface, and a circuit for sensing a continuity of the loop.

Also, there is disclosed a method for detecting erosion of a wear surface of a component. The method comprises the steps of providing at least one cavity in the component, inserting a sensor in the at least one cavity, the sensor comprised of at least one signal relaying loop embedded in the component and comprising a wear portion positioned at a wear distance from the wear surface and during operation, sensing a continuity of the at least one loop.

Other objects, advantages and features of the present invention will become more apparent upon reading of the following non-restrictive description of illustrative embodiments thereof, given by way of example only with reference to the accompanying drawings.

DETAILED DESCRIPTION OF THE ILLUSTRATIVE EMBODIMENTS

Figure 1A:
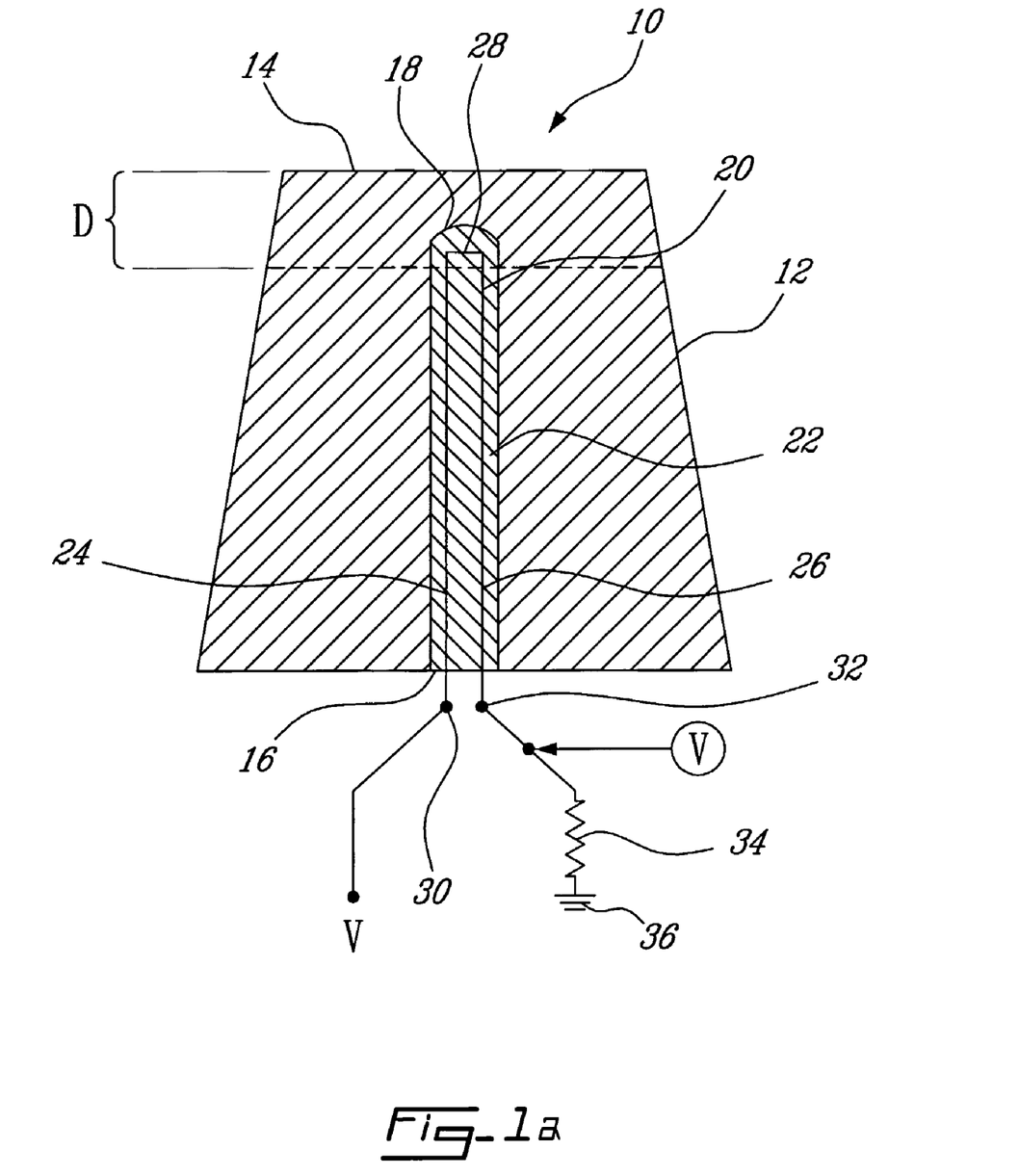
FIGS. 1A and 1B disclose a wear sensor in accordance with an illustrative embodiment of the present invention.

Referring to FIG. 1A, an illustrative embodiment of a wear sensor in accordance with an illustrative embodiment of the present invention. The wear sensor, generally referred to using the reference numeral 10, is comprised of a component 12 in which wear is to be sensed. The component has at least one wear surface 14 which will be slowly eroded through, for example, contact with abrasive articles or the like (not shown). A cavity 16 is machined or otherwise shaped into the component 12 with the tip 18 of the cavity 16 being positioned in proximity to the wear surface 14. A signal carrying loop 20 is inserted into the cavity 16 and secured therein using a filler material (or matrix) 22. The filler material 22, for example, is a non-conductive self hardening compound such as epoxy resin or the like.

In an alternative embodiment, the loop 20 could be directly moulded into the component 12 during fabrication, or comprise a lamination applied to the component 12.

Still referring to FIG. 1A, the signal relaying loop 20 is comprised of a pair of segments 24, 26 interconnected by a wear portion 28 toward the ends of the pair of segments 24, 26. In this regard, the wear portion 28 is the portion of the loop 20 which will be worn away with increased wear of the wear surface 14 of the component 12. In the present illustrative embodiment the wear portion 28 is manufactured from the same materials as the pair of segments 24, 26, for example, from a 24 gauge copper wire which is simply bent over on itself prior to insertion into the cavity 16 (although in an alternative illustrative embodiment the wear portion 28 could be manufactured from a different signal carrying material, such as a thicker or thinner gauge copper wire, etc.). Use of a small gauge wire or the like as the element allows the size of the cavity 16 to be reduced, thereby lessening the impact machining of the cavity 16 may have on the structural integrity of the component in which the wear is being tested. Additionally, with components 12 under a lot if stress such as lifters used in mills, it has been found that providing for a plurality of cavities as in 16 can weaken the component 12 considerably, especially if the cavities as in 16 are arranged along the same line. Therefore, care should be taken to ensure that the cavities as in 16 are properly placed, for example in a staggered configuration.

In order to aid in maintaining the pair of segments 24, 26 and the wear portion 28 electrically isolated from one another along their lengths, a wire having an insulating jacket could also be used. The ends of the pair of segments 24, 26 of the loop 20, which project beyond the filler material; 22, provide an easily accessible pair of contacts 30, 32.

In operation, the state of the signalling paths is determined by sensing, using a suitable circuit (not shown), whether a signal transmitted via one contact 30 is received by a receiver attached to the other contact 32. Illustratively, this is determined by measuring the resistance between the contacts 30, 32 (for example, by applying a voltage V, or alternatively a current, to one of the contacts 30, 32 and measuring the voltage across a resistor 34 placed between the other contact and ground 36). If the resistance is suddenly increased, then this is an indication that the pair of segments 24, 26 have been isolated from one another (i.e. the loop 20 has been damaged and is no longer continuous).

Figure 1B:
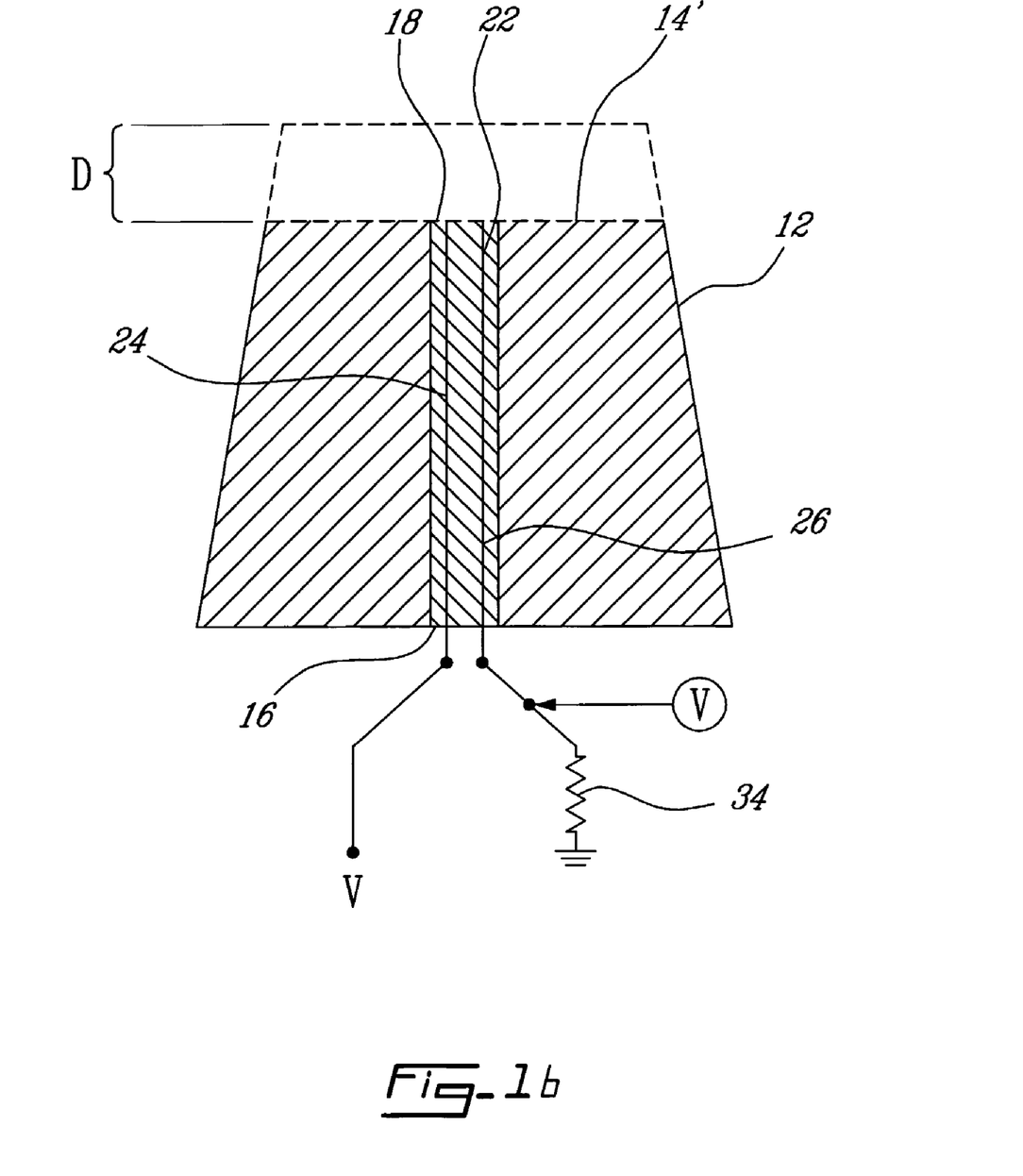

Referring now to FIG. 1B in addition to FIG. 1A, as the wear surface 14 is eroded, the tip 18 of the cavity 16 will eventually be exposed. Further erosion of the wear surface 14 will cause the filler material 22 also to be eroded. When the erosion of the wear surface 14 has progressed to the level of the element 20, the pair of segments 24, 26 will become isolated from one another due to the removal of the wear portion 28. As will now be apparent to a person of ordinary skill in the art, isolation of the pair of segments 24, 26 from one another will cause the voltage across the resistor 34 to drop to the ground 36, thereby providing and indication that the erosion of the wear surface 14 has reached depth (wear distance) D in the region of the loop 20.

In an alternative embodiment, the pair of segments 24, 26 and the wear portion 28 could be fabricated from an optic fibre. In this regard, instead of a voltage/resistance network or the like placed across the ends of the pair of segments 24, 26 for sensing isolation of the segments 24, 26 from one another, a light emitting and sensing network would be used (not shown).

Figure 2:
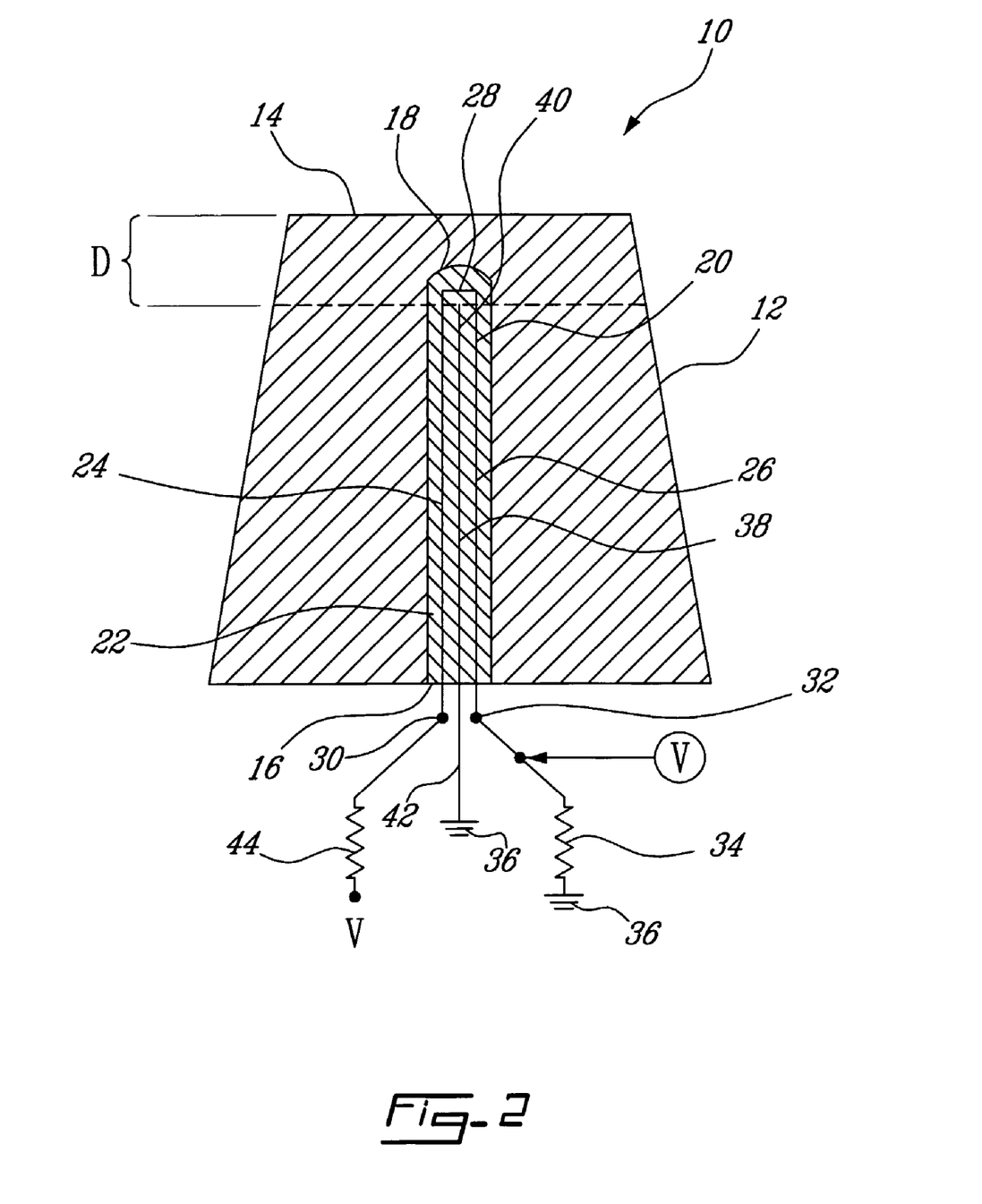
FIG. 2 discloses a wear sensor in accordance with a first alternative illustrative embodiment of the present invention.

Referring now to FIG. 2, a wear sensor 10 in accordance with an alternative embodiment of the present invention will now be described. In environments where the wear surface 14 is in contact with erosive materials which are also capable of conducting electricity, for example erosive slurries comprised of one or more ionic salts suspended in an aqueous medium, erosive removal of the wear portion 28 may not result in the isolation of the pair of segments 24, 26 from one another. In order to overcome this limitation, a second isolated conductive element 38 is inserted into the cavity 16 together with the original conductive loop 20 such that a first end 40 of the second conductive element 38 is located in proximity to the tip 18 of the cavity 16. The original conductive element 20 and the second conductive element 38 are then secured therein using the filler material 22 leaving the ends of the original conductive loop 20 exposed thus providing a pair of contacts 30, 32 and leaving the second end 42 of the second conductive element 38 exposed, thus providing a third contact.

Still referring to FIG. 2, as the wear surface 14 is eroded to depth (or wear distance) D the wear portion 28 will be removed and the ends of the pair of segments 24, 26 and the second conductive element 38 exposed. By coupling a sufficiently large resistor 34 between the contact 32 and ground 36 and coupling the second end 42 to ground 36 (thus effectively grounding the second conductive element) the majority of the current flowing along the first segment 24 (a the amount of current which follows a given path is inversely proportional to the resistance of that path) will flow via the second conductive element 38 to ground 36. Once again, by measuring the voltage across the resistor 34, a drop in voltage will indicate that the erosion of the wear surface 14 has reached depth (wear distance) D in the region of the conductive loop 20 and damaged the conductive loop 20. Additionally, in order to protect against short circuit of the voltage source V, provision of a second resistor 44 between the voltage source V and the contact 30 may also be provided for.

Figure 3:
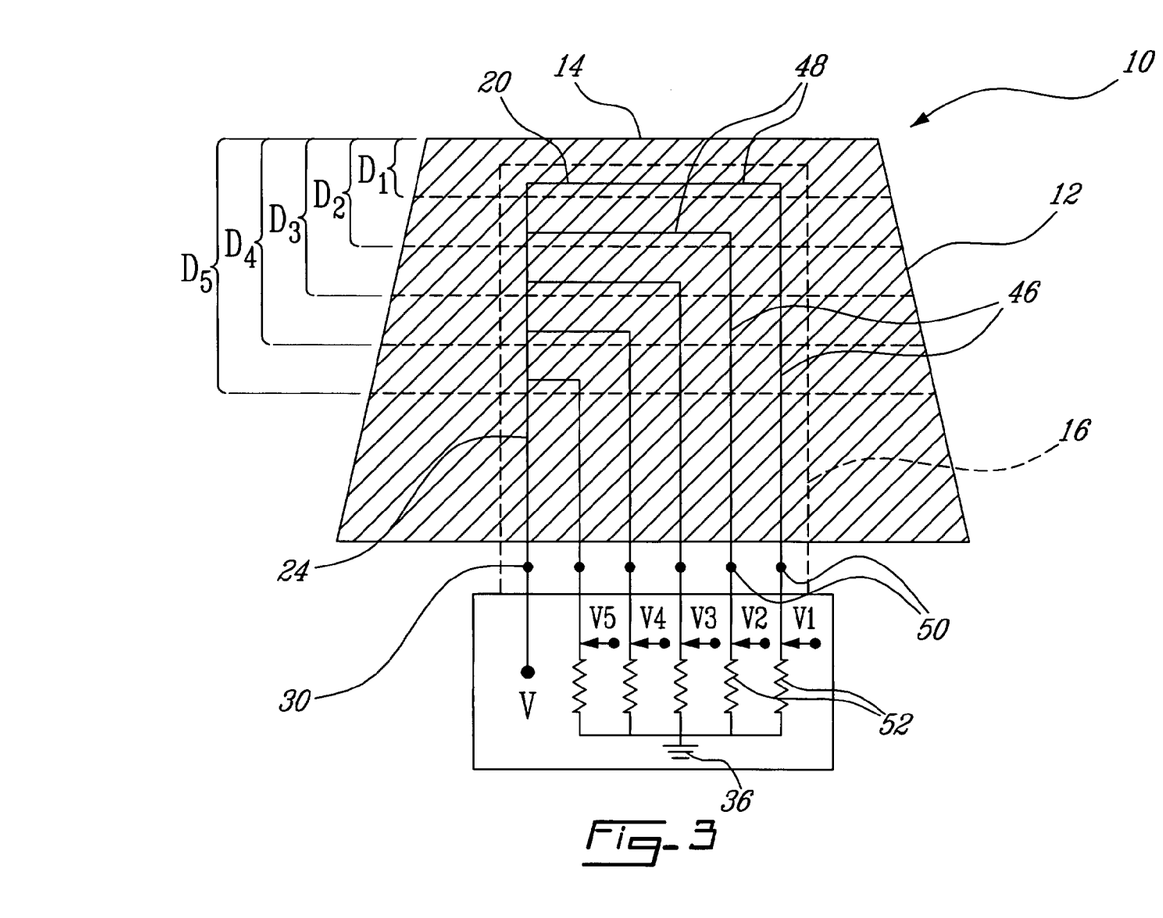
FIG. 3 discloses a wear sensor in accordance with a second alternative illustrative embodiment of the present invention.

Referring now to FIG. 3, a wear sensor 10 in accordance with a second alternative illustrative embodiment will now be described. In applications where it is wished to determine the amount of wear on a wear surface 14 of a component 12, provision of a single conductive loop 20 comprised of a first conductor and a second conductor may prove insufficient. In order to overcome this limitation, a conductive loop 20 comprised of a first segment 24 and a series of second segments as in 46 and wear portions as in 48 is provided for. The wear portions as in 48 are arranged vis-à-vis the wear surface 14 such that erosion of the wear surface 14 will cause the second segments as in 46 to be successively isolated from the first segment 24 by successive wearing away of the wear portions as in 48. As will now be appreciated by one of ordinary skill in the art, by measuring the resistance between the end 30 of the first segment 24 and the ends as in 50 of the second segments as in 46, for example by supplying voltage V (or current) to the first conductor and measuring the voltage across a series of resistors as in 52 placed between the ends as in 50 of the second segments as in 46 and ground 36, the erosion of the wear surface 14 can be determined at a number of different depths (wear distances) $D_1$, $D_2$, $D_3$, etc.

Figure 4A:
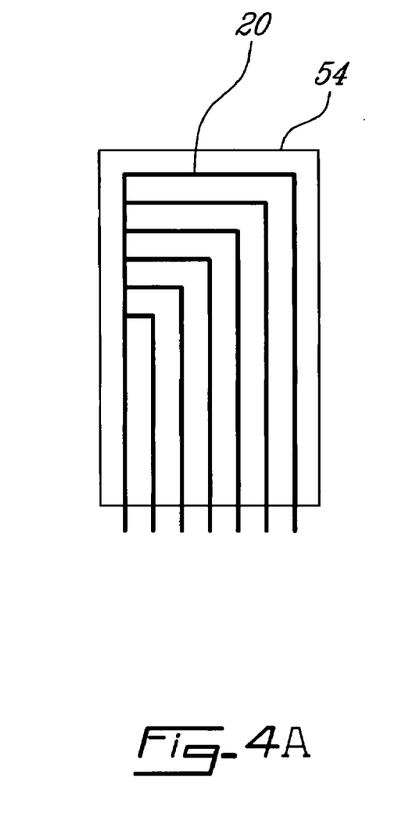
FIGS. 4A and 4B disclose a printed wear sensor in a accordance with an illustrative embodiment of the present invention.

Referring now to FIG. 4A in addition to FIG. 3, in order to simplify and provide more accurate placement of the conductive loop 20 within the opening 16 in the component 12, the element 20 can be patterned using, for example, a conductive trace, for example a copper film, on a suitable substrate 54, resulting in a printed conductive circuit. The substrate 54 can then be fastened to a non-wear internal or external surface intersecting the wear surface (for example, perpendicular to the wear surface 14) using a suitable bonding technique such as an epoxy resin adhesive or the like, or laminated into the component 12 during fabrication. In a particular embodiment the substrate 54 can be manufactured from a flexible material, such as polyester or polyamide and the like, thereby allowing the substrate to be laminated into or fastened to the surface of irregular shaped objects. Additionally, referring to FIG. 4B, alternatively, the flexible printed medium could be rolled up to form a tube and inserted into the cavity 16 and secured therein using a suitable filler material 22, such as non-conductive epoxy resin, or the like. In this regard, in order to simplify insertion of the substrate 54 into the cavity, the substrate can be rolled around a small rod 56, for example manufactured from a non-conductive material such as plastic or the like. Additionally, the substrate 54 can be bonded to the rod 56 prior to insertion to further simplify ease of installation.

Figure 4B:
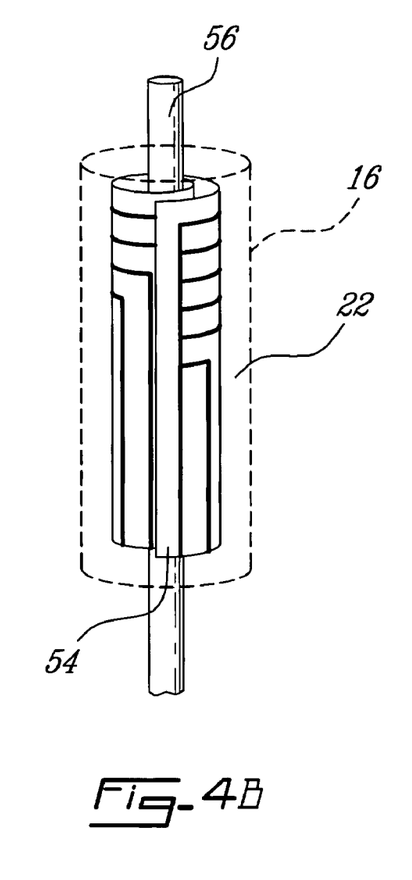

It is also foreseeable that, instead of using the flexible printed circuit as described hereinabove, micro/nano fabrication techniques could be applied to a substrate patterned with a conductive material (such as those used for the fabrication of microchips).

Figure 5:
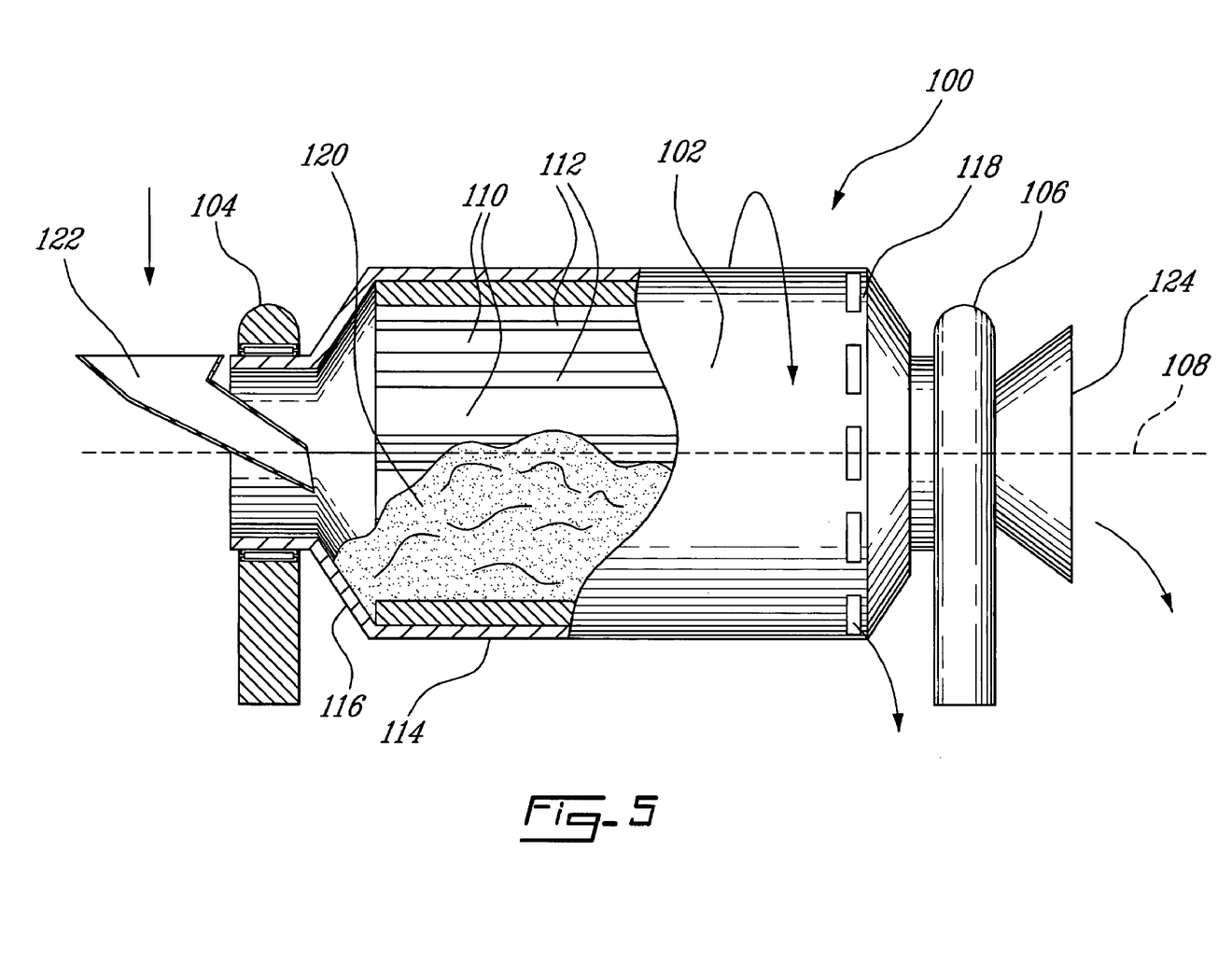
FIG. 5 discloses a ball mill.
Figure 6A:
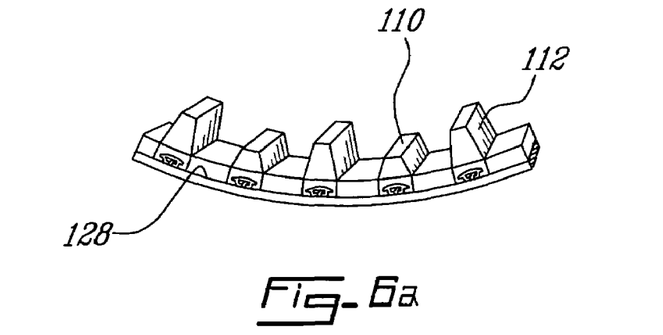
FIGS. 6A through 6D disclose various lifter profiles for use in a mill.
Figure 6B:
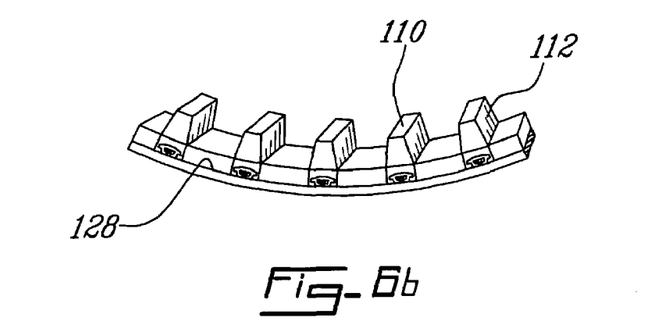
Figure 6C:
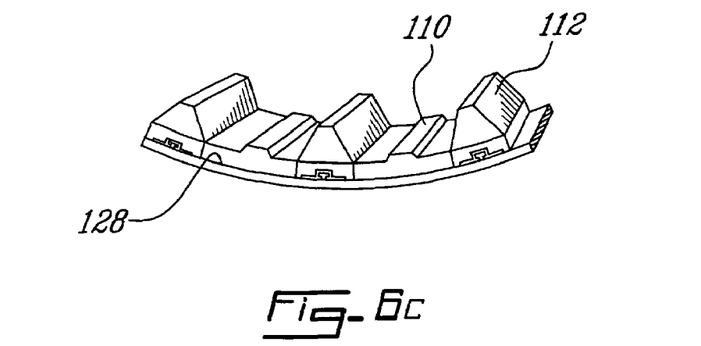
Figure 6D:
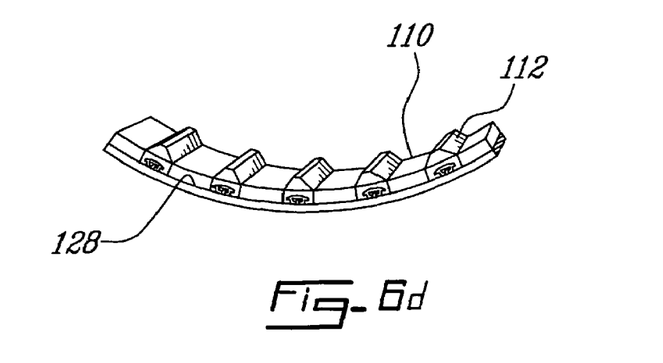

Referring to FIG. 5, an illustrative application of the present invention in the mining industry will now be described. One important step in liberating minerals from ore bearing rock is milling the rock. Most ores contain the valuable metals disseminated in a matrix of less valuable rock called gangue. It is therefore necessary to separate valuable minerals from the gangue to yield a product that has a much higher content of the valued material. Following the initial mining step, ore is typically reduced in size by the crushing and/or grinding circuit, and the target mineral is concentrated by various methods. Ore milling typically refers to a specific subset of concentrating operations and is the focus of the present illustrative application.

Milling operations typically utilise a mill (such as a SAG, AG, rod or ball mill), generally referred to using the reference numeral 100, which is comprised of a large drum 102 suspended at either end by a pair of supports 104, 106. Typical drum diameters range from about 2 meters to 12 meters. The drum 102 is capable of rotating around its axis 108 which is parallel to the ground. Rotation of the drum 102 is typically provided by a motor and, as necessary, a geared drive or the like (both not shown). The inside surfaces of the drum is lined with liners 110 and lifters 112. The lifters 112 have a raised profile and protrude towards the centre of the drum 102. Lifters 112 along the drums sides are arranged longitudinally in parallel with the axis of rotation 108. Lifters 112 along the charging end 116 or discharging end 118 are arranged radially to the axis of rotation 108. Course feedstock ore 120 is fed into the drum 102 by an infeed assembly 122. Rotation of the drum 102 serves to lift the feed stock ore 120 which is then allowed to drop from a significant height. Three mechanisms cause the breakdown of the feedstock ore 120: impact due to the fall of the ore onto the charge below; attrition of smaller particles between larger grinding bodies; and abrasion (or rubbing off) of particles from the larger bodies. Additionally, steel or ceramic balls or metal rods are sometimes added to the feedstock in order to aid the reduction process. Milled ore progresses towards along the drum and is discharged via the trunnion 124 or one of a number of peripheral discharges 126.

Referring now to FIGS. 6A through 6D in addition to FIG. 5, the lifters 112 can have a variety of different profiles depending on the ore being milled and milling process being used. Additionally, the lifters 112 can be manufactured from a variety of different materials such as rubber, cast iron, steel and other materials such as ceramics and composites. As the milling process is largely abrasive, especially the lifters 112 are subject to a significant degree of wear. Additionally, this wear is typically uneven over the length of the mill drum 102. In some cases at the discharge end of the mill 118 wear of liners can be such that slurry racing occurs which leads to accelerated wear, compromise of the liner and possible wear of the shell itself. As such the lifters 112 must be frequently inspected and exchanged as necessary. This typically requires stopping and in some cases emptying the drum 102 which, as the milling process is a continuous process, can lead to significant inefficiencies in the use of the mill 100.

Figure 7A:
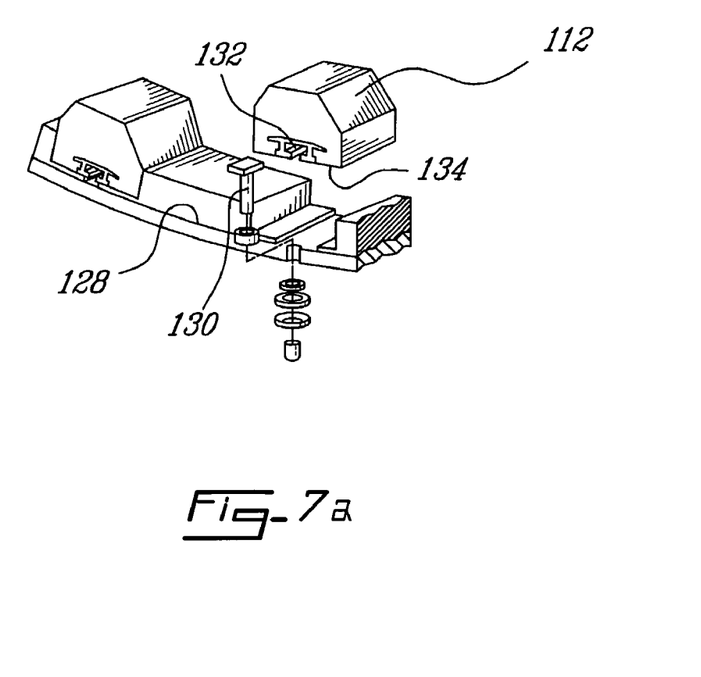
FIGS. 7A and 7B disclose the application of the wear sensor in a lifter for use in a mill in accordance with an illustrative embodiment of the present invention.
Figure 7B:
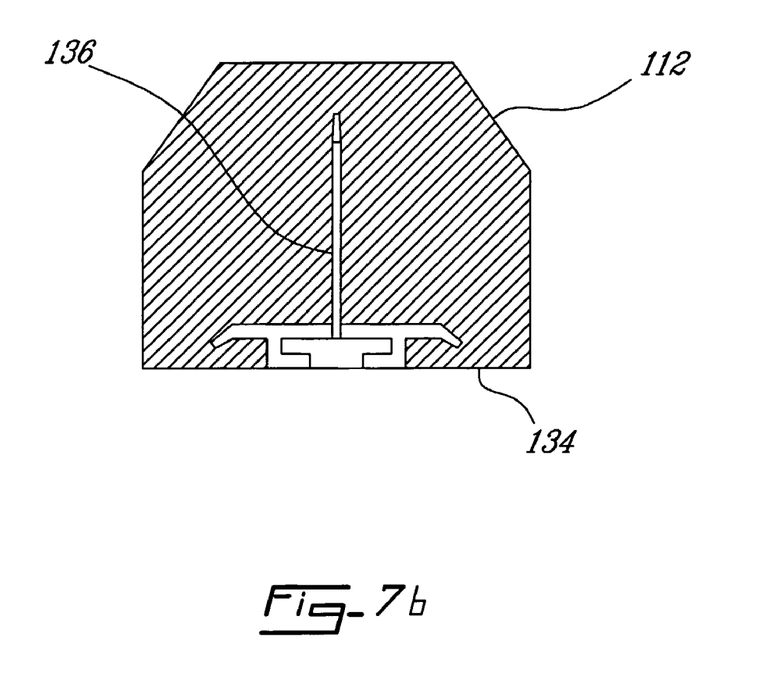

Referring now to FIG. 7A, in order to secure the lifters 112 to the inner surface 128 of the drum 102, typically a nut and bolt assembly comprised of, for example, a T-bolt 130 which is inserted into a corresponding slot 132 on the rearward surface 134 of the lifter 112 is used. Referring now to FIG. 7B, by machining a small opening 136 through the slot 132 and into the rearward surface 134 of the lifter 112 a opening for the insertion of the conductive element(s) as described hereinabove can be provided for. Once the opening is filled and suitable contact points provided for, the lifter 112 can be fastened to the inner surface 128 of the drum 102. It will now be apparent to a person of ordinary skill in the art that, with provision of signal relaying interconnections between the contact points and a suitable apparatus for measuring the status of these signal relaying paths, the wear of the lifters 112 beyond certain predetermined amounts can be determined without the necessity of halting the mill. Additionally, a series of small cavities as in 136 could be machined or otherwise formed along the length of the rearward surface 134 of the lifter 112 and elements inserted and secured therein in order to provide sensing of wear over the length of the lifter 112. The cavities as in 136 need not be in a straight line. Indeed, as discussed above it is preferable that any cavities made in the lifter 112 be out of alignment in order to reduce the introduction of stress points in the lifter 112.

Figure 8:
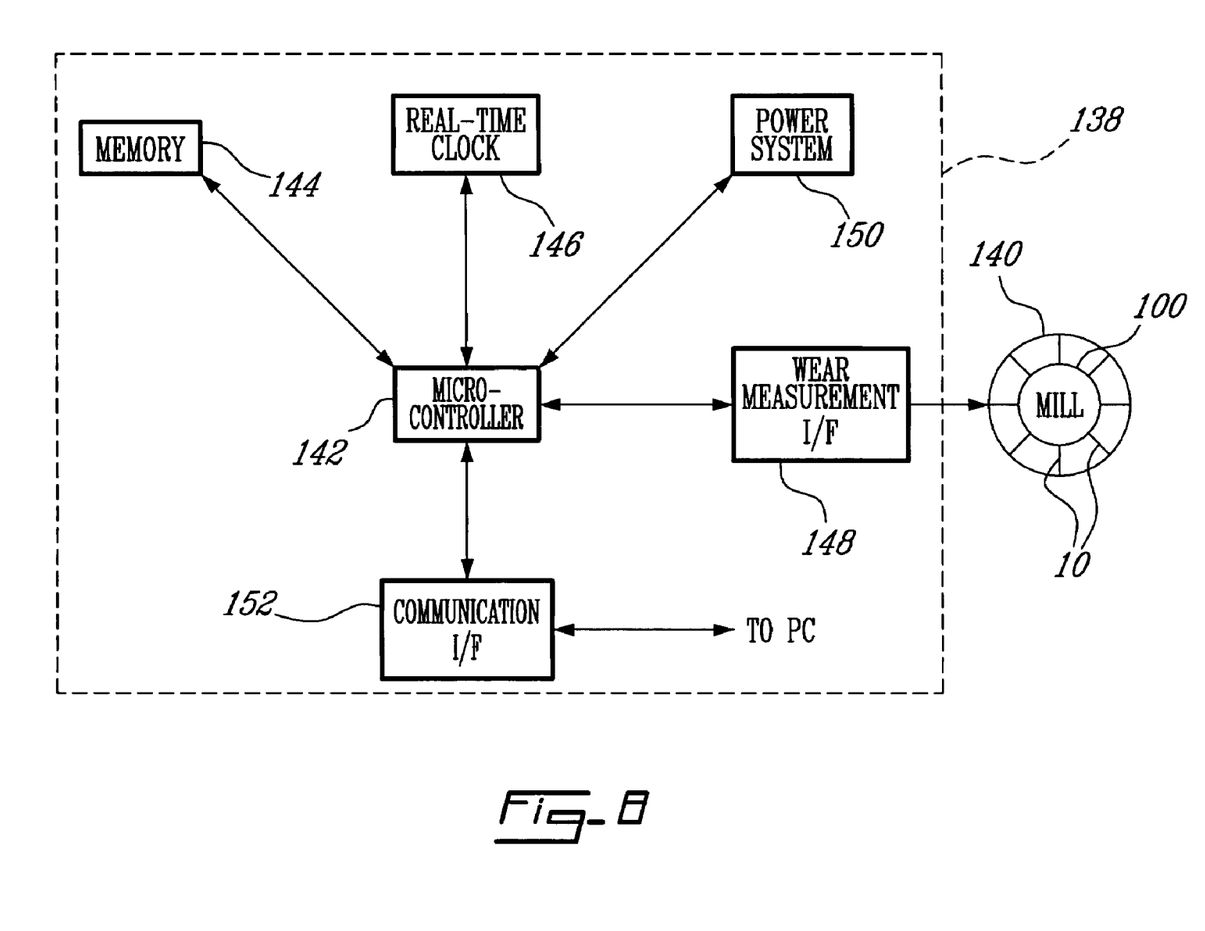
FIG. 8 is a schematic diagram of a microprocessor controlled measuring set-up in accordance with an illustrative embodiment of the present invention.

Referring to FIG. 8, in order to measure the wear of lifters (reference 112 in FIG. 5) in a mill 100, a microprocessor controlled measuring set-up 138 was developed for interfacing with a network 140 of wear sensors 10 embedded within lifters in the mill 100. The measuring set-up 138 was comprised of a microcontroller 142, a memory 144 (for example ROM and/or RAM) and a Real Time Clock 146. In order to take readings from the individual sensors 10 of the wear sensor network 140 ringing the mill 100, a wear measurement interface 148 was provided. Additionally, a power module 150 was provided to supply power to both the microcontroller 142 and the wear sensor network 140. Also, in order to allow measurements collected from the wear sensor network 140 to be further analysed, as well as to provide some control over the microcontroller 142, a serial communications interface 152 was provided to an external PC (not shown). Illustratively, in operation the microcontroller 142 continually reads each sensor of the wear sensor network 140. If a sensor is worn, the microcontroller 142 flags the sensor as being worn, for example by assigning to that sensor a value of 1. Similarly, if the sensor is not worn a value of 0 is assigned to the sensor variable. The microprocessor 142 forms a binary number with the values of the individual bits being provided by the sensor values. In this regard, the first sensor value provides the first bit, the second sensor value provides the second bit, etc. It will be apparent now to a person of ordinary skill in the art that the current status of all the sensors in the sensor network 140 can be determined simply by examining the binary number. Once formed, the binary number, along with the current time provided by the real-time clock 146, can be stored in memory 144 for later examination or transmitted to the external PC via the communications interface 150.

It is to be understood that the invention is not limited in its application to the details of construction and parts illustrated in the accompanying drawings and described hereinabove. The invention is capable of other embodiments and of being practised in various ways. It is also to be understood that the phraseology or terminology used herein is for the purpose of description and not limitation. Hence, although the present invention has been described hereinabove by way of preferred embodiments thereof, it can be modified, without departing from the spirit, scope and nature of the subject invention.

What is claimed is:

1. A sensor for detecting erosion of a wear surface of a component, the sensor comprising:
   at least one conductive trace on a substrate, said substrate attached to the component such that a wearing portion of said trace between a first trace end and a second trace end comes within a predetermined distance from the wear surface; and
   a circuit for sensing when said first end is isolated from said second end;
   wherein the component is manufactured from a material selected from the group consisting of rubber, cast iron, steel and ceramics or combinations thereof.

2. The sensor of claim 1, wherein said substrate is embedded in the component.

3. The sensor of claim 1, wherein the component comprises a second non-wear surface intersecting the wear surface, and wherein said substrate is fastened to the non-wear surface.

4. The sensor of claim 3, further comprising an adhesive for fastening said substrate to the non-wear surface.

5. The sensor of claim 2, wherein said substrate is laminated into the component.

6. The sensor of claim 2, wherein the component comprises a cavity machined therein and further comprising a filler material for retaining said substrate in the cavity.

7. The sensor of claim 6, wherein said filler material is an epoxy.

8. The sensor of claim 1, wherein said substrate is a PCB.

9. The sensor of claim 8, wherein said PCB is flexible.

10. The sensor of claim 9, wherein said flexible PCB is rolled up.

11. The sensor of claim 10, wherein said rolled up flexible PCB is retained in a cavity machined in the component.

12. The sensor of claim 9, further comprising a rod for supporting said flexible PCB, and wherein said flexible PCB is wound around said rod.

13. The sensor of claim 12, further comprising an adhesive bonding said flexible PCB to said rod.

14. The sensor of claim 13, wherein said rolled up flexible PCB is retained in the cavity using a filler material.

* * * * *